(12) United States Patent
Zhang et al.

(10) Patent No.: US 9,629,362 B1
(45) Date of Patent: Apr. 25, 2017

(54) METHODS FOR KILLING INSECTS USING METHYL BENZOATE

(71) Applicant: The United States of America, as represented by the Secretary of Agriculture, Washington, DC (US)

(72) Inventors: Aijun Zhang, Laurel, MD (US); Yan Feng, Bowie, MD (US)

(73) Assignee: THE UNITED STATES OF AMERICA, AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 0 days.

(21) Appl. No.: 14/988,090

(22) Filed: Jan. 5, 2016

(51) Int. Cl.
*A01N 37/10* (2006.01)

(52) U.S. Cl.
CPC .................................... *A01N 37/10* (2013.01)

(58) Field of Classification Search
CPC ........................................................ A01N 37/10
See application file for complete search history.

(56) References Cited

U.S. PATENT DOCUMENTS 8,394,358 B2 * 3/2013 Schneidmiller ........ A01N 65/00
424/43

OTHER PUBLICATIONS

Eaton et al. Controlling Wasps, Bees and Hornets, (2016), University of New Hampshire.*

* cited by examiner

*Primary Examiner* — Yong Chu
(74) *Attorney, Agent, or Firm* — G. Byron Stover; John D. Fado

(57) ABSTRACT

A method for killing insects, involving treating an object or area with an insect killing effective amount of a composition containing methyl benzoate and optionally a carrier.

18 Claims, 5 Drawing Sheets

METHODS FOR KILLING INSECTS USING METHYL BENZOATE

BACKGROUND OF THE INVENTION

Disclosed are methods for killing insects, involving treating an object or area with an insect killing effective amount of a composition containing methyl benzoate and optionally a carrier.

Several studies have suggested that, as result of world population growth, increasing global food demand for direct human consumption poses huge challenges for the sustainability of crop production (Alexandratos, N., Proc. Natl. Acad. Sci. USA, 96: 5908-5914 (1999); Cassman, K. G., Proc. Natl. Acad. Sci. USA, 96: 5952-5959 (1999); Tilman, D., et al., Nature, 418: 671-677 (2002)). Although about 99% of agricultural crop pests in the world are control by natural enemies (Debach, P., and D. Rosen, Biological Control by Natural Enemies, 2nd edition, London: Cambridge University Press, 1991)), agricultural crop production is still severely reduced in the range of 25-50% by insects, weeds, and pathogens (Pimentel, D., et al., Bioscience, 41: 402-409 (1991)). Application of synthetic pesticides in pest control has been shown to provide significant economic benefits, allowing farmers to reduce human labor costs in crop production and have made it possible to produce a great volume of food for global consumers (Pimentel et al. 1991). However, synthetic pesticide usages cause serious damage to human health, agriculture, and natural ecosystems. Over 98% of sprayed insecticides and 95% of herbicides reach destinations other than their target species because they are sprayed or spread across entire agricultural fields, resulting in detriment of wildlife and the environment (Miller, G. T., Sustaining the Earth: An integrated Approach, 6th edition, page 386, Pacific Grove: Brooks/Cole, 2004)). Recent estimates suggest that pesticides account for more than 20,000 human fatalities yearly, and that most of these will have occurred in developing countries (Forget, G., J. Toxicol. Environ. Health, 32: 11-31 (1991)). Thus, there is an urgent need to curtail pesticide use and reduce the human and environmental impacts of synthetic pesticides.

Over the past twenty years, botanic pesticides as attractive alternatives to synthetic pesticides have received the most acclaim and shown growing recognition in pest management due to less threat to human health and the environment (Isman, M. B., Annu. Rev. Entomol., 51: 45-66 (2006); de Oliveira, J. L., et al., Biotechnol. Adv., 32: 1550-1561 (2014); Adorjan, B., and G. Buchbauer, Flavour Fragrance J., 25: 407-426 (2010)). A number of botanical pesticides based on pyrethrum and neem have successfully been commercialized and used in agricultural and veterinary pest control; however, it only commands little more than 1% of the global pesticide market (Isman, M. B., Crop Protect., 19: 603-608 (2000)).

Thus there is still significant opportunity for development of botanical pesticides as environmental-friendly alternatives and utilization in pest management. We have found that methyl benzoate (MB), a volatile organic compound (VOC) component identified from fermented apple juice, is an insecticide.

SUMMARY OF THE INVENTION

Disclosed herein are methods for killing insects, involving treating an object or area with an insect killing effective amount of a composition containing methyl benzoate and optionally a carrier.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

DETAILED DESCRIPTION OF THE INVENTION

Figure 1:
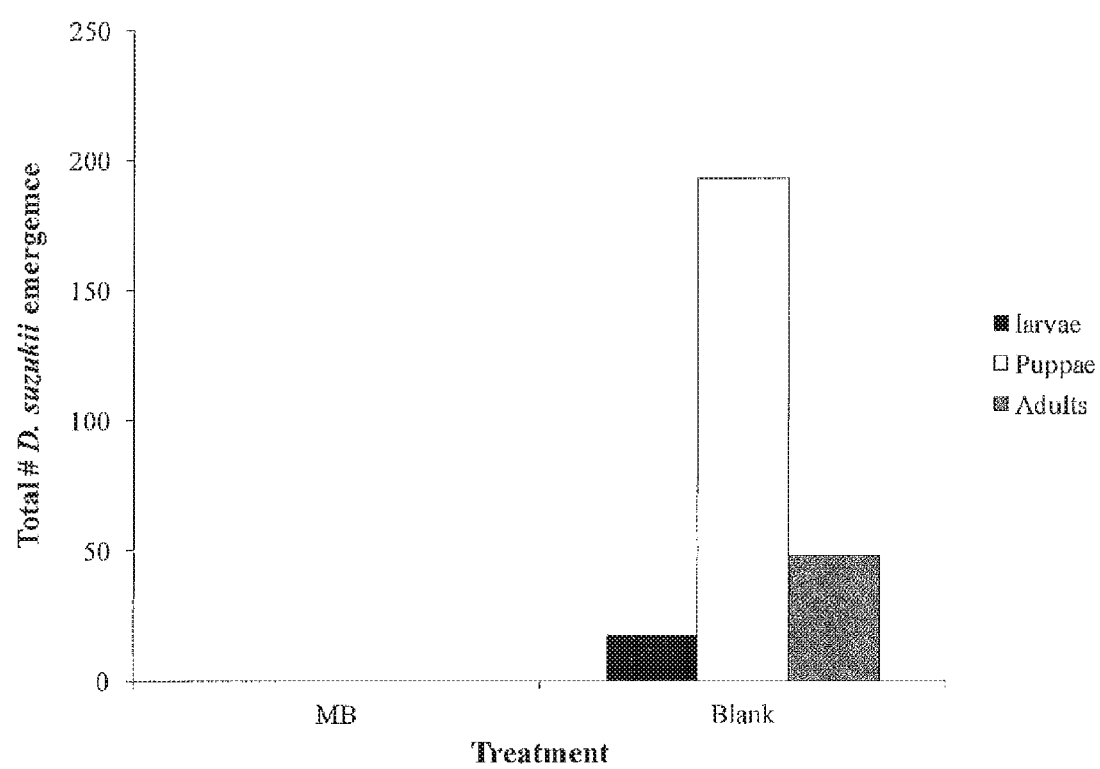
FIG. 1 shows impact of MB on emergence of *Drosophila suzukii* from pre-infested blueberries (100 berries pre-infested with 100 mixed-adult for 4 days/treatment, 50 berries were then soaked with 1% MB solution and water respectively for 2 hr; N=2) as described below. Assessment was conducted after 10 days incubation at room temperature.

As part of an effort aimed at development of green pesticides based on plants, potential acute toxicity and sublethal effect of MB against *D. suzukii* has been investigated by us, comparing with some monoterpenes in which the toxicities had been well demonstrated against several different insect pests. These monoterpenes include $\alpha$-terpinene (Palacios, S. M., et al., Molecules, 14: 1938-1947 (2009)), $\gamma$-terpinene (Batish, D. R., et al., For. Ecol. Manage., 256: 2166-2174 (2008)), $\alpha$-terpineol (Isman 2000), $\alpha$-pinene (Traboulsi, A. F., et al., Pest Manage. Sci., 58: 491-495 (2002)), and 1,8-cineole (Pavlidou, V., et al., J. Agric. Urban Entomol., 21: 39-49 (2004)). Among tested VOCs, MB was surprisingly found to be the most acutely toxic for *D. suzukii*. MB was also investigated against several other pest species, including brown marmorated stinkbug *Halyomorpha halys*, diamondback moth *Plutella xylostella*, and tobacco hornworm *Manduca sexta* for its acute toxic efficacy or sublethal effect. Our results surprisingly showed that the methyl benzoate not only could effectively prevent eggs from hatching and inhibited nymph and/or larvae developments of *H. halys, P. xylostella*, and *M. sexta* with contact ovicidal effect, but also had significant fumigant and contact insecticidal action against insects such as *H. halys* nymphs.

Thus disclosed herein are methods for killing insects, involving treating an object or area with an insect killing effective amount of a composition containing methyl benzoate and optionally a carrier. The terms "object" or "area" as used herein include any place where the presence of target pests is not desirable, including any type of premises, which can be out-of-doors, such as in farms, orchards, parks, yards, gardens, lawns, tents, camping bed nets, camping areas, forests, and so forth, or indoors, such as in barns, garages, commercial buildings, homes, and so forth, or any area where pests are a problem, such as in shipping or storage containers (e.g., luggage, bags, boxes, crates, etc.), packing materials, bedding, and so forth; also includes clothing.

The amount of the compounds (e.g., methyl benzoate) or compositions (e.g., containing methyl benzoate) used will be at least an effective amount. The term "effective amount," as used herein, means the minimum amount of the compounds or compositions needed to kill the insects when compared to the same area or object which is untreated. Of course, the precise amount needed will vary in accordance with the particular composition used; the type of area or object to be treated; and the environment in which the area or object is located. The precise amount of the composition can easily be determined by one skilled in the art given the teaching of this application. For example, one skilled in the art could follow the procedures utilized below; the composition would be statistically significant in comparison to a negative control. Generally the concentration of MB will be about 0.025% to about 10% (e.g., 0.025 to 10%, for example in an aqueous solution), preferably about 0.5% to about 4% (e.g., 0.5 to 4%), more preferably about 1% to about 2% (e.g., 1 to 2%). The composition may or may not contain a control agent for insects, such as a biological control agent or an insecticide known in the art to kill insects. Other compounds (e.g., insect attractants known in the art) may be added to the composition provided they do not substantially interfere with the intended activity and efficacy of the composition; whether or not a compound interferes with activity and/or efficacy can be determined, for example, by the procedures utilized below.

The compositions optionally contain a carrier or carrier material known in the art (e.g., agronomically or physiologically or pharmaceutically acceptable carrier). The carrier component can be a liquid or a solid material. As is known in the art, the vehicle or carrier to be used refers to a substrate such as a membrane, hollow fiber, microcapsule, cigarette filter, gel, polymers, septa, or the like. All of these substrates have been used to release insecticides in general and are well known in the art. Suitable carriers are well-known in the art and are selected in accordance with the ultimate application of interest. Agronomically acceptable substances include aqueous solutions, glycols, alcohols, ketones, esters, hydrocarbons halogenated hydrocarbons, polyvinyl chloride; in addition, solid carriers such as clays, cellulosic and rubber materials and synthetic polymers.

The compositions can therefore be used for killing insects such as harmful or troublesome blood-sucking, stinging and biting insects, ticks and mites. The term insects as used herein include all stages of insect life cycle: adults, larvae, nymphs, pupae, and eggs. The term insects as used herein include non-insects such as ticks, mites, spiders, centipedes, scorpions, and solifugids.

Agriculturally important insects (e.g., insects that are harmful to agricultural plants and/or products) include spotted wing drosophila *Drosophila suzukii*, brown marmorated stinkbug *Halyomorpha halys*, emerald ash borer *Agrilus planipennis*, gypsy moth *Lymantria dispar dispar*, pink hibiscus mealybug *Maconellicoccus hirsatus*, Mediterranean fruit fly *Ceratitis capitata*, plum curculio *Conotrachelus nenuphar*, diamondback moth *Plutella xylostella*, soybean aphid *Aphis glycines*, cotton aphid *Aphis gossypii*, indianmeal moths *Plodia interpunctella*, bean weevils *Acanthoscelides obtectus*, mountain pine beetle *Dendroctonus ponderosae*, and tobacco hornworm *Manduca sexta*.

Blood-sucking insects include mosquitoes (for example *Aedes, Culex* and *Anopheles* species), sand flies (for example *Phlebotomus* and *Lutzomyia* species such as *Phlebotomus papatasi*), owl gnats (*Phlebotoma*), blackfly (*Culicoides* species), buffalo gnats (*Simulium* species), biting flies (for example *Stomoxys calcitrans*), tsetse flies (*Glossina* species), horseflies (*Tabanus, Haematopota* and Chrysops species), house flies (for example *Musca domestica* and *Fannia canicularis*), meat flies (for example *Sarcophaga carnaria*), flies which cause myiasis (for example *Lucilia cuprina, Chrysomyia chloropyga, Hypoderma bovis, Hypoderma lineatum, Dermatobia hominis, Oestrus ovis, Gasterophilus intestinalis* and *Cochliomyia hominovorax*), bugs (for example *Cimex lectularius, Rhodnius prolixus* and *Triatoma infestans*), lice (for example *Pediculus humanus, Haematopinus suis* and *Damalina ovis*), louse flies (for example *Melaphagus orinus*), fleas (for example *Pulex irritans, Cthenocephalides canis* and *Xenopsylla cheopis*) and sand fleas (for example *Dermatophilus penetrans*).

Biting insects include cockroaches (for example *Blattella germanica, Periplaneta americana, Blatta orientalis* and *Supella supellectilium*), beetles (for example *Sitophilus granarius, Tenebrio molitar, Dermestes lardarius, Stegobium paniceum, Anobium puntactum* and *Hylotrupes bajulus*), termites (for example *Reticulitermes lucifugus*), bed bug (for example *Cimex lectularius*) and ants (for example *Lasius niger*).

Ticks include, for example, *Ornithodorus moubata, Ixodes ricinus, Boophilus microplus* and *Amblyomma hebreum*, and mites include, for example, *Varroa destructor, Sarcoptes scabiei, Dermanyssus gallinae, Tetranychus urticae, Tetranychus cinnabarinus*, and *Oligonychus pratensis*.

Preferably, the blood-sucking and biting insects, ticks and mites include mosquitoes, sand flies, biting flies (e.g., black flies, biting midges), bed bugs, ticks, and fire ants (genus *Solenopsis*; for example black imported fire ants, *S. richetri*).

"Optional" or "optionally" means that the subsequently described event or circumstance may or may not occur, and that the description includes instances in which said event or circumstance occurs and instances where it does not. For example, the phrase "optionally comprising a defoaming agent" means that the composition may or may not contain a defoaming agent and that this description includes compositions that contain and do not contain a foaming agent.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

Unless defined otherwise, all technical and scientific terms used herein have the same meaning as commonly understood by one of ordinary skill in the art to which the invention belongs. As used herein, the term "about" refers to a quantity, level, value or amount that varies by as much as 30%, preferably by as much as 20%, and more preferably by as much as 10% to a reference quantity, level, value or amount. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Chemicals: Methyl benzoate, α-terpinene, γ-terpinene, terpineol, cineole, α-pinene, Tween 20, and Tween 80 were purchased from Sigma-Aldrich (St. Louis, Mo.). Acetone was used as solvent and purchased from Sigma-Aldrich (St. Louis, Mo.). All chemicals were used without further purification. Commercial pesticides were purchased from Home Depot (College Park, Md.) and used directly: Spectracide® Bug Stop (St. Louis, Mo.), Bayer Advanced® Carpenter Ant & Termite Killer Plus (Research Triangle Park, N.C.), Hot Shot® Bedbug & Flea Home Insect Killer (St. Louis, Mo.), Raid Max® Bug Barrier (Racine, Wis.), Amdro Quick Kill® Lawn & Landscape Insect Killer (Atlanta, Ga.), Ortho® Bug B Gon (Marysville, Ohio), Natria® Insect Disease & Mite Control (Research Triangle Park, N.C.), Bayer Advanced® Complete Insect Killer (Research Triangle Park, N.C.), Ortho® Flower, Fruit & Vegetable Insect Killer (Marysville, Ohio), Sevin® Garden Tech (Atlanta, Ga.), EcoSmart® Organic Home Pest Control (Roswell, Ga.), and EcoSmart® Organic Garden Insect Killer (Roswell, Ga.). The active ingredients (AI) and corresponding concentrations for the above commercial pesticides are listed in Table 2.

Insects: The *H. halys* adults, nymphs, and eggs were obtained from colony maintained in a USDA-ARS, facility located in Beltsville, Md. The *H. halys* colony was established in 2007 from adults collected in Allentown, Pa. Insects were reared on a diet of organic green beans and shelled sunflower and buckwheat seeds (2:1, w/w) in ventilated plastic cylinders and maintained in Percival incubator at 25° C. and 60% RH, under a 16L:8D photoperiod (Khrimian, A., et al., J. Nat. Prod., 77: 1708-1717 (2014)). Eggs were collected weekly and hatched in plastic Petri dishes with a water vial, and after molting to second-instars, the nymphs were transferred to ventilated plastic cylinders for the remaining four instars (Khrimian et al. 2014). Adult males and females were separated 1 or 2 days after emergence and subsequently maintained in different containers.

The colony of *M. sexta* was reared and maintained on an artificial wheat germ diet (Yamamoto, R. T., J. Econ. Entomol., 62: 1427-2431 (1969)) in an insectary located in the same USDA Beltsville facility at 24° C. and 40% RH. Eggs and young larvae were covered by glass trays. Older larvae were kept in ventilated plastic boxes (27×17.5×10 cm, BioQuip Inc., Rancho Dominguez, Calif.). Adults were kept in screened cages (45.75×45.75×45.75 cm, BioQuip). After small tomato plants were introduced into the screened cages for 3-4 days, deposited eggs on the plants were removed by hand.

The *P. xylostella* colony was reared and maintained on an artificial wheat germ diet (Shelton, A. M., et al., J. Entomol. Sci., 26: 17-26 (1991)) at the same USDA facility. Eggs and larvae were put in closed cardboard cups (236 mL, 8.9 cm diameter, 5.7 cm height, Solo Cup Company, Lake Forest, Ill.) and kept in an incubator (Percival Scientific Inc., Perry, Iowa) at 25° C., 34% RH, under a 16L:8 D photoperiod in the same insectary. Adults were maintained in screened cages (30.5 cm×30.5 cm×30.5 cm, BioQuip Inc). Eggs were deposited on aluminum foil strips (approx. 5.0×30.5 cm) dipped in cabbage juice and collected after 3-4 days.

The *D. suzukii* colony was provided by Rutgers University. Colony was reared on cornmeal diet (Dalton, D. T., et al., Pest Manage. Sci., 67: 1368-1374 (2011)) in polystyrene vials with plugs and kept in a Percival incubator at 25° C., 34% RH, under a 16L:8 D photoperiod in the same USDA Beltsville facility.

Organic green beans and blueberries (Cottle Farms, Cottle Strawberry Nursery, Inc, Faison, N.C.) were purchased from MOM'S organic market (College Park, Md.).

Laboratory bioassay: Bioassays were conducted in USDA Beltsville laboratory at 25° C., 60% RH, under a 16L:8D photoperiod with ~1700 lux light illuminance. A fume hood was maintained at same conditions with face velocity at 129 FPM. The plastic cups (32 oz, diameter 4.5 inches, deep 5 inches, or 16 oz, diameter 4.5 inches, deep 2.5 inches) were purchased from papermart.com (CA). The cover was cut into a 80 mm diameter hole and glued with an 85 mm diameter Nylon screen mesh (81×81 per inch) mesh size, BioQuip, CA). The polystyrene vials (height 95 mm, diameter 28.5 mm) and plugs were obtained from Fisher Scientific (Pittsburg, Pa.). The plastic cage (30×30×30 cm) was purchased from BugDorm (Rancho Dominguez, Calif.). Glass vial (20 mL), glass spray bottle (Amber glass with spray top, 30 mL), Petri dish (9 cm diameter), and Whatman filter paper (90 mm diameter) were obtained from VWR (Atlanta, Ga.). Deionized water (DI) containing 1% emulsifier (v/v), Tween 20 and Tween 80, at 1.1 ratio was used to make different VOCs water solutions and also used as blank control.

Impact of MB on *D. suzukii* control: To investigate the acute toxicity of MB against *D. suzukii*, 100 blueberries were placed in a plastic cage (30×30×30 cm) and infested by 100 mixed sex adult *D. suzukii* for 4 days. After removal of all insects, half of pre-infested blueberries were dipped in 100 mL MB aqueous emulsion at designated concentration, while the other half of pre-infested blueberries was dipped in DI water as control for 2 h. Then the blueberries were separately placed in two Petri dishes and allowed to air dry for 2 h. The blueberries were stored in two plastic cups (32 oz) incubated at room temperature for 10 days. Present of adults were then subsequently assessed and development of larvae and pupae was further inspected by dissection of the berries. The experiment was repeated twice.

Evaluation of MB and other VOCs as oviposition deterrent against *D. suzukii*: To examine the oviposition deterrent property of MB and other essential oils against *D. suzukii*, 10 blueberries were separately dipped in 100 mL MB or other essential oil aqueous emulsions at 1% concentration for 2 h. Another 10 blueberries were dipped in 100 mL DI water for 2 h as control. The blueberries were separately placed on different Petri dishes and allowed to air dry for 2 h. After a Petri dish containing 10 treated blueberries was put into a plastic cup (32 oz), 10 mixed sex adults *D. suzukii* were subsequently introduced into each cup. Mortality of the *D. suzukii* was examined after 48 h. After removing all insects, the blueberries were maintained at room temperature for another 10 days. Present of adults were subsequently assessed and development of larvae and pupae was further inspected by dissection of the berries.

Toxicity of MB against *H. halys* nymphs: The bioassays were carried out in glass vials (20 mL). Filter paper was cut into round shaped pieces (2.4 cm diameter). 50 µL MB acetone solution with different concentrations was loaded onto the filter paper evenly, and the filter paper was dried for 1 min and then put into the bottom of the vial. A small piece of green bean was put on the filter paper in the vial as food source. Different stages of *H. halys* nymphs were introduced into the vial and capped with a cotton ball. For each stage, 30 nymphs were used for each amount of MB loading. For the nymphs of the first instar, 10 nymphs were put into 1 vial. For the nymphs of the second and third instar, 5 nymphs were put into 1 vial. For the nymphs of the fourth instar, 3 nymphs were put into 1 vial. For the nymphs of the fifth instar, 2 nymphs were put into 1 vial. The mortality was assessed after 24 hr. Mortality data was subjected to probit analysis using PoloPlus for $LC_{50}$, $LC_{95}$ with 95% confidence intervals calculation.

Ovicidal toxicity of MB and commercial pesticides: The aqueous solutions of MB with designated concentrations and commercially available pesticides with different concentrations of active ingredient (AI) were separately stored in glass spray bottles. The eggs (10 for *H. halys* and *M. sexta*, 100 for *P. xylostella*) were laid on filter papers in Petri dishes. Different aqueous solutions were sprayed on the surfaces of different eggs three times (~0.5 mL) to completely cover the treatment areas. Then Petri dishes were covered with lids and maintained in a fume hood for 10 days. The Petri dishes were then inspected for presence of nymph/larvae development or numbers of unhatched eggs.

Data analysis: Comparisons of different treatments were analyzed using one-way ANOVA followed by Ryan-Eibot-Gabriel-Welsch F test (SPSS 10.0 for Windows (George, D., and P. Mallery, SPSS for Windows step by step: A simple guide and reference, 4th edition, Allyn & Bacon, 2002)) for significance at $\alpha=0.05$. PoloPlus software (LeOra Software, Berkeley, Calif.) was used to conduct probit analysis for mortality data, and $LC_{50}$ and $LC_{95}$ with 95% confidence intervals were estimated.

Insecticidal activity: MB surprisingly exhibited potent toxicity in controlling *D. suzukii*. Direct application of MB at 1% concentration on 4 days pre-infested blue berries surprisingly caused complete mortality and no larvae and pupae developed or adult flies emerged after 10 days incubation at room temperature (FIG. 1). MB also surprisingly showed fumigant and contact nymphcidal effects against *H. halys* nymphs at the different stages with $LC_{50}$ values from 1.01 to 2.39 µL/vial (Table 1).

Figure 2:
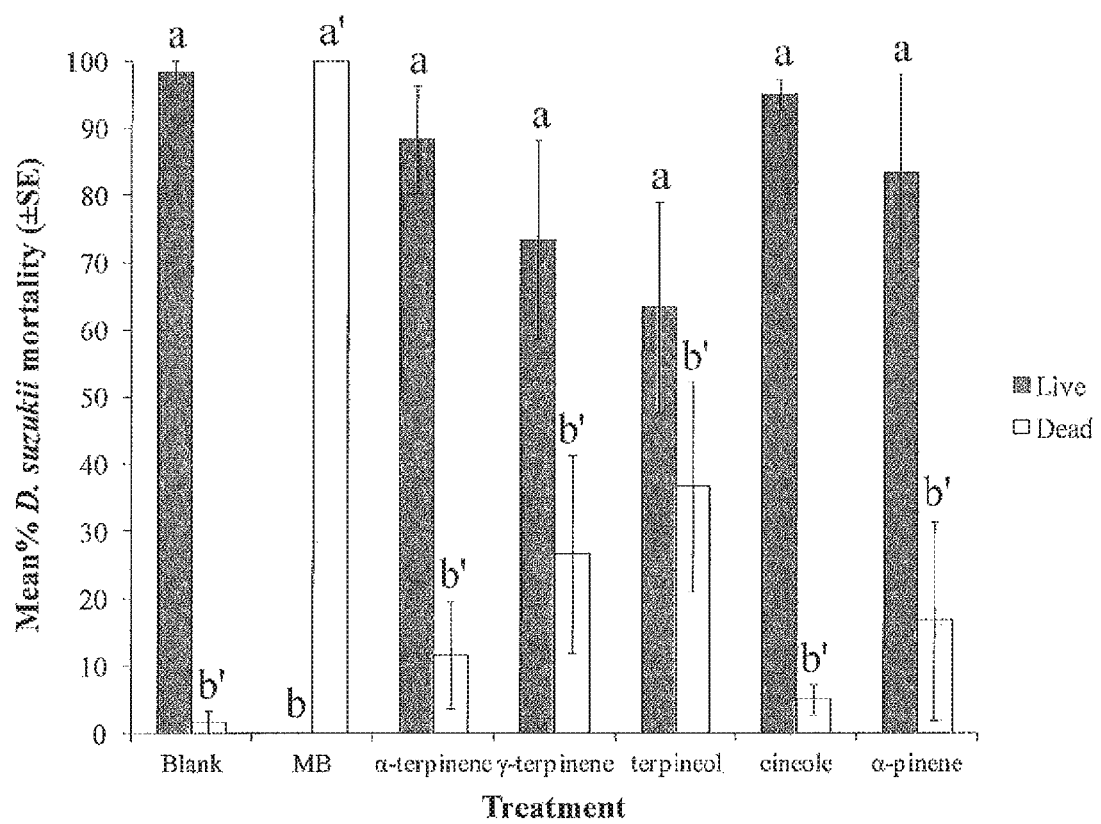
FIG. 2 shows impact of different VOCs against adult *D. suzukii* (60 files/treatment). Mortality assessed after 48 hrs exposure to pre-treated blueberries (60 berries/treatment, 1% solution soaking for 2 hr) as described below. Means flowed by the different letters and superscript are significantly different at $\alpha=0.05$ (N=6, F=10.691; df=6,35, p<0.0001).
Figure 3:
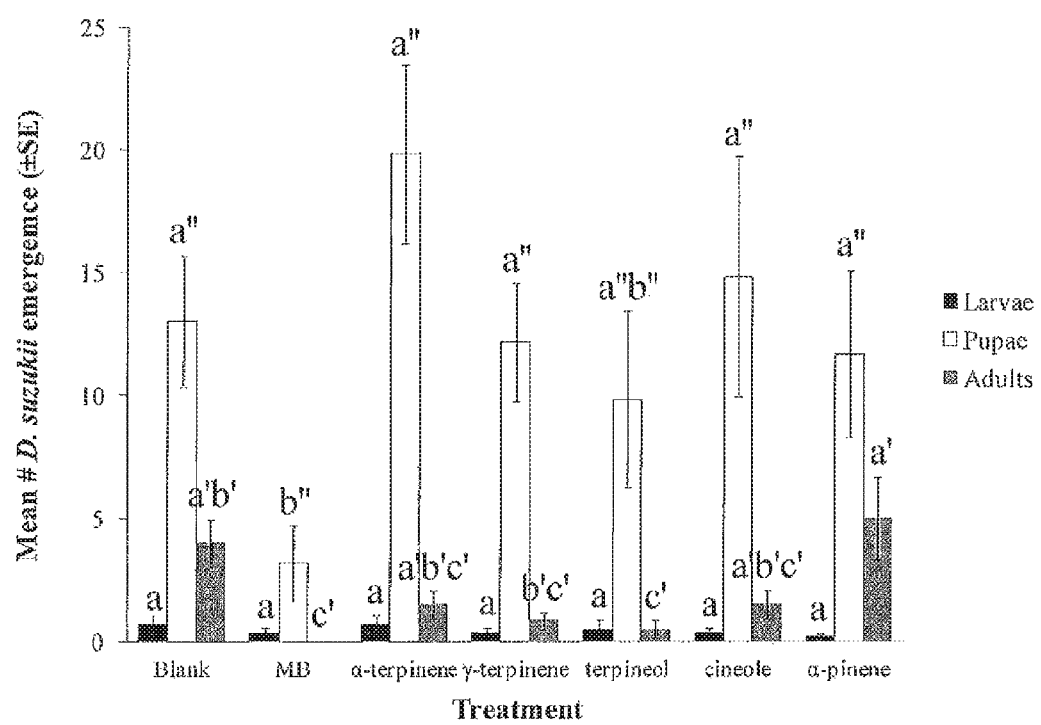
FIG. 3 shows impact of different VOCs on subsequent *D. suzukii* infestation and development on pre-treated blueberries. Numbers assessed after 10 days incubation at room temperature as described below. Means flowed by the different letters and superscripts are significantly different at $\alpha=0.05$ (Log transformed; N=6, df=6,35; for larvae, F=0.248, p>0.05; for pupae, F=3.586, p<0.01; for adult, F=4.843, P<0.01).

Oviposition deterrent activity: Of the VOCs tested (1% solution), MB surprisingly exhibited the most toxicity against *D. suzukii*. MB surprisingly caused complete mortality and no adult flies survived after 2 days exposure to pre-treated blueberries (FIG. 2) (N=6, F=10.691; df=6,35, p<0.0001). All monoterpene VOCs tested did not show significant toxicity compared with blank control. Following subsequent further incubation at room temperature for 10 days, surprisingly no adults emerged and significantly fewer pupae developed from MB treated berries compared with blank control and all other essential oil treatments (FIG. 3; N=6, df=6,35; for adult, F=4.843, p<0.01; for pupae, F=3.586, p<0.01), indicating that MB also surprisingly possessed strong oviposition deterrent property.

Figure 4:
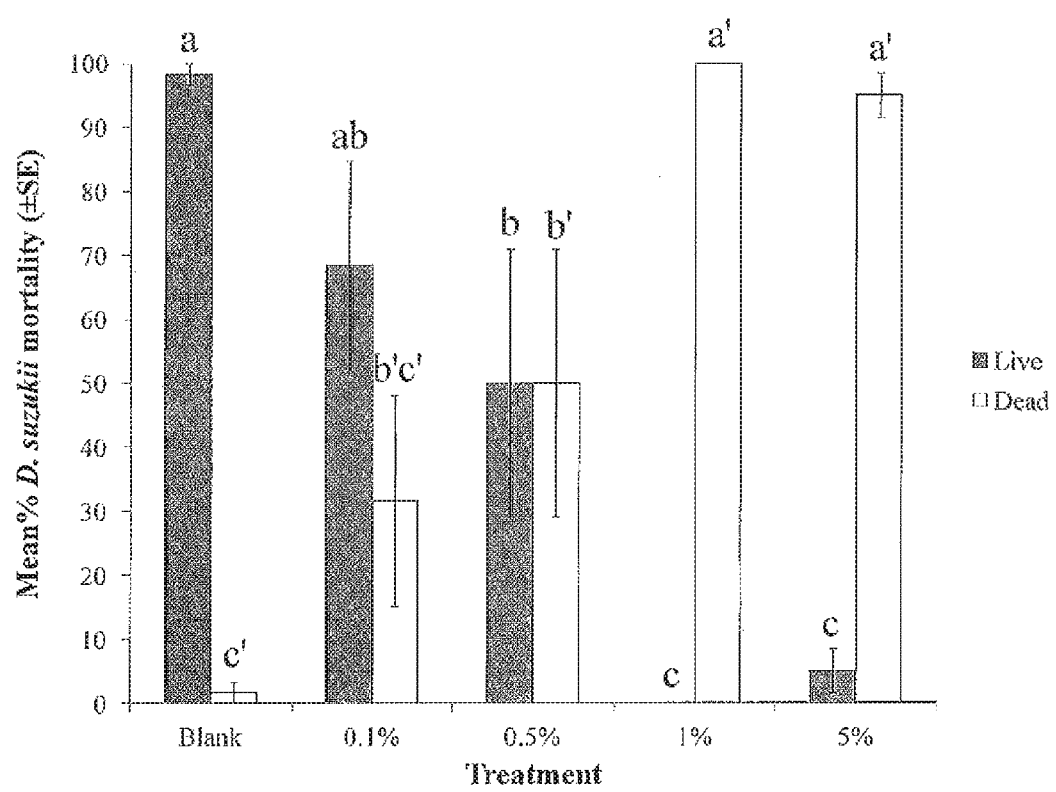
FIG. 4 shows dose response of MB against adult *D. suzukii* (60 files/treatment). Mortality assessed after 48 hrs exposure to pre-treated blueberries (60 berries/treatment, soaking for 2 hr) as described below. Means flowed by the different letters and superscripts are significantly different at $\alpha=0.05$ (N=6, F=12.151; df=4,25, p<0.0001).
Figure 5:
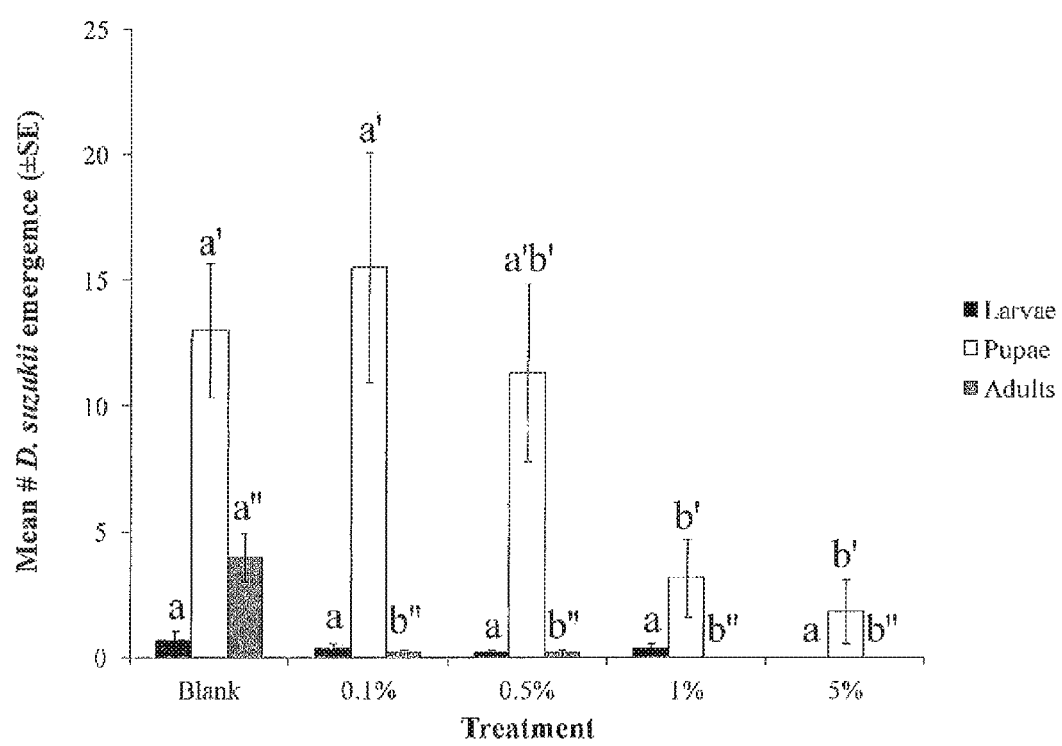
FIG. 5 shows impact of MB with different doses on subsequent *D. suzukii* infestation and development on pre-treated blueberries. Numbers assessed after 10 days incubation at room temperature. Means flowed by the different letters and superscripts are significantly different at $\alpha=0.05$ (Log transformed; N=6, df=4,25; for larvae, F=0.458, p>0.05; for pupae, F=5.982, p<0.01; for adult, F=27.981, p<0.001).

The oviposition deterrent property of MB is concentration dependent. After 2 days exposure to pre-treated blueberries, MB surprisingly exhibited potent activity against adult *D. suzukii* at 1% and 5% concentrations. Little activity at 0.5% and no significant activity at 0.1% concentrations were observed (FIG. 4, N=6, F=12.151; df=4,25, p<0.0001). Following subsequent further incubation at room temperature for 10 days, surprisingly no adults emerged and significantly fewer pupae developed from 1% and 5% MB treated berries compared with the blank control (FIG. 5, N=6, df=6,35; for adult, F=27.981, p<0.001; for pupae, F=5.982, p<0.01; for larvae, F=0.458, p>0.05).

Ovicidal toxicity: The ovicidal action of MB was evaluated by measuring hatchability in direct spray bioassay on eggs of three species of insects, including *H. halys*, *M. sexta*, and *P. xylostella*. The toxicity was compared with some commercially available organic pest control products containing essential oil and some synthetic pyrethroid, neonicotinoids, sulfur, or carbamate pesticides (Table 2). Our results indicated that the MB surprisingly had potent larvicidal effects with an $LC_{50}$ value at 0.020 mg/cm$^2$ and $LC_{95}$ value at 0.048 mg/cm$^2$ on *H. halys* (Table 3). Surprisingly lower dosage of MB (0.0637 mg/cm$^2$ active ingredient) was needed to reach 100% egg mortality for *H. halys* compared to neonicotinoids/pyrethroid (imidacloprid/β-cyfluthrin, 0.0688 mg/cm$^2$) (Table 4). At 0.0318 mg/cm$^2$, MB was surprisingly as potent as deltamethrin (0.0019 mg/cm$^2$), ζ-cypermethrin (0.0223 mg/cm$^2$), carbaryl (0.0080 mg/cm$^2$), pyrethroid (β-cyfluthrin, 0.1592 mg/cm$^2$), sulfur/pyrethroid (surfur/pyrethrin, 0.6525 mg/cm$^2$), and one of the organic essential oil products (2-phenethyl propionate, clover oil, rosemary oil, and thyme oil, at 0.3979 mg/cm$^2$). Commercially available pesticides, λ-cyhalothrin (0.0016 mg/cm$^2$), and acetamiprid (0.0004 mg/cm$^2$) and another organic essential oil product tested containing rosemary oil and peppermint oil (0.0637 mg/cm$^2$) were almost ineffective.

The MB was surprisingly also a potent toxic agent against *M. sexta* eggs at 0.0637 mg/cm$^2$ dose with an $LC_{50}$ value at 0.015 mg/cm$^2$ and $LC_{95}$ value at 0.060 mg/cm$^2$ (Table 3). Surprisingly it was significantly better than the mixture of bifenthrin & ζ-cypermethrin (0.0239 mg/cm$^2$) and an essential oil product containing 2-phenethyl propionate, clover oil, rosemary oil, and thyme oil (0.3979 mg/cm$^2$) (Table 4).

For *P. xylostella*, MB surprisingly demonstrated potent ovicidal activity at as low as 0.0032 mg/cm$^2$ dose (Table 4) with an $LC_{50}$ value at 0.001 mg/cm$^2$ and $LC_{95}$ value at 0.005 mg/cm$^2$ (Table 3). Interestingly, the carbaryl was one of the most effective compounds against *H. halys* egg at 0.0080 mg/cm$^2$, but it was one of the most ineffective ovicidal compounds against *P. xylostella* (Table 4).

Discussion: The research described above clearly demonstrated that methyl benzoate was surprisingly a very efficient green pesticide against invasive insect pest *D. suzukii* compared with some known insecticidal essential oil components. Surprisingly it not only effectively prevented *D. suzukii* from oviposition and inhibited subsequent larvae/pupae development, but also caused complete mortality of adult flies on pre- and post-treated blueberries at as low as 1% concentration. Moreover, methyl benzoate surprisingly also possessed excellent ovicidal toxicity against several different species of eggs compared with some commercially available pesticides. On the basis of toxicity data, MB was surprisingly 5 times more toxic than the conventional pyrethroid (β-cyfluthrin), 20 times more toxic than sulfur & pyrethrin mixture, and 12 times more toxic than one of the organic commercial products (2-phenethyl propionate, clover oil, rosemary oil, and thyme oil) against *H. halys* eggs.

Nether γ-cyhalothrin nor acetamiprid exhibited ovicidal toxicity against *H. halys* at tested doses. For *M. sexta* and *P. xylostella*, surprisingly similar toxic results were obtained, but *P. xylostella* appeared to be more sensitive to MB treatment. To reach 100% egg mortality, surprisingly only 0.0064 mg/cm$^2$ was needed, which was 10 times less than *H. halys* and 20 times less than *M. sexta* eggs needed for the same results.

In nature, many plant species emit a great amount of VOCs into atmosphere, which are related with plant ecology, physiology, and atmospheric chemistry (Lerdau, M. et al., Bioscience, 47: 373-383 (1997); Guenther, A., et al., J. Geophys. Res. Atmos., 100: 8873-8892 (1995)). Some VOCs may act as defensive compounds against insect herbivores and plant pathogens; while others may act as chemical signals involved in plant-plant, plant-animal, and plant-microorganisms interactions (Penuelas, J., and J. Llusia, Biol. Plant., 44: 481-487 (2001)), although it is not possible to predict which VOCs are effective. Methyl benzoate is among one of VOCs that naturally occurs as aroma and scent of many plants (Choudhary, M. I., et al., Phylochemistry, 69: 1018-1023 (2008)), flowers (Knudsen, J. T., and L. Tollsten, Bot. J. Linn, Soc., 113: 263-284 (1993); Effmert, U., et al., Phytochemistry, 66: 1211-3230 (2005)), and fruits (Froehlich, O., and P. Schreier, Flavour Fragrance J., 4: 177-184 (1989); Shaw, G. J., et al., J. Sci. Food Agric., 34: 743-747 (1983); Young, H., et al., J. Sci. Food Agric., 34: 81-85 (1983); Bartley, J. P., and A. M. Schwede, J. Agric. Food Chem., 37: 1023-1025 (1989); Binder, R. G., and R. A. Flath, J. Agric. Food Chem., 37: 734-736 (1989); Muchalal, M., and J. Crouzet, Agric. Biol. Chem,. 49: 1583-1589 (1985)), and plays important roles in plant communication with the surrounding environment. Particularly, methyl benzoate is one of the most abundant floral scents emitted from petunia, *Petunia hybrid*, and snapdragon flower, *Antirrhinum majus*, and functions as a long-range attractant to lure bees for pollination (Kolosova, N. et al., Plant Cell, 13; 2333-2347 (2001); Heinrich, B., Bumblebee Economics: With a New Preface, Cambridge: Harvard University Press, 2004); Dudareva, N., et al., Plant Cell, 12: 949-961 (2000); Negre, F., et al., Plant Cell, 15: 2992-3006 (2003)). Methyl benzoate has also been used by many insect species as a semiochemical that carries a message for the purpose of communication between individuals of the same species (intraspecific) or between different species (interspecific) (El-Sayed, A. M., The pherobase: database of insect pheromones and semiochemicals (2015)). Moreover, methyl benzoate is known for its sweet, balsamic, spicy, and heady floral odor; and it has been used as a fragrance ingredient and preservative in many personal care applications, such as shampoos, shower products and face/neck cure, liquid soaps, mouthwash, perfume, hair colorants and cosmetics (European-Commission, List of preservatives allowed in cosmetic products (2015)). Methyl benzoate is of low to moderate human toxicity by ingestion and inhalation (Clayton, G. D., and F. E. Clayton, Patty's Industrial Hygiene and Toxicology: Volume 2A, 2B, 2C: Toxicology, 3 edition, New York: John Wiley Sons (1981-1982); Opdyke, D. L. J., Monographs on Fragrance Raw Materials: A Collection of Monographs Originally Appearing in Food and Cosmetics Toxicology, pp. 356, Oxford: Pergamon Press Ltd., 1979)). It is approved by the US Food and Drug Administration (21 CFR 172.515) and the European Union (EU Regulation 1334/2008 & 178/2002) for food use and is commercially available as food-grade flavor ingredients from many chemical companies. In industry, methyl benzoate is used as an organic solvent. It also is environmentally friendly. In the atmosphere, methyl benzoate will slowly biodegrade without much difficulty (Atkinson, R., Int. J. Chem. Kinet., 19: 799-828 (1987)). However, to the best of our knowledge, pesticiual activity of methyl benzoate has not been previously reported. Overall, our research findings demonstrated that methyl benzoate was surprisingly an effective green pesticide against some invasive species, especially, *H. halys* and *D. suzukii*, with low concentration and high mortality; therefore, providing an alternative of synthetic pesticide for insect pest management in crop production.

All of the references cited herein, including U.S. Patents, are incorporated by reference in their entirety.

Thus, in view of the above, there is described (in part) the following:

A method for killing insects, said method comprising (or consisting essentially of or consisting of) treating an object or area with an insect killing effective amount of a composition comprising (or consisting essentially of or consisting of) methyl benzoate (as sole insecticide) and optionally a carrier. Methyl benzoate is generally the only volatile organic compound (VOC) component (from fermented apple juice) utilized in the method, thus other VOCs in fermented apple juice are generally not utilized in the method. The above method, wherein said composition contains a carrier.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Nymphcidal toxicity of MB to different stages of *H. halys*

| Stage | n* | LC$_{50}$ (95% CL) μL/vial | Slope ± SE |
|---|---|---|---|
| 1$^{st}$ | 270 | 1.03 (0.93-1.10) | 7.69 ± 1.07 |
| 2$^{nd}$ | 270 | 1.01 (0.86-1.12) | 6.73 ± 1.11 |
| 3$^{rd}$ | 270 | 1.23 (1.12-1.33) | 5.28 ± 0.60 |
| 4$^{th}$ | 270 | 2.39 (2.19-2.60) | 6.10 ± 0.72 |
| 5$^{th}$ | 270 | 1.77 (1.60-1.93) | 6.00 ± 0.67 |

*Number of nymphs tested.

TABLE 2

Commercially available pesticides tested in laboratory bioassay.

| Trademark | Product | Active Ingredient (AI) | C %* |
|---|---|---|---|
| Spectracide ® | Bug Stop | Gamma-cyhalothrin | 0.025 |
| Bayer Advanced ® | Carpenter Ant & Termite Killer Plus | Beta-cyfluthrin | 2.5 |
| Hot Shot ® | Bedbug & Flea Home Insect Killer | Lambda-cyhalothrin | 0.03 |
| RaidMax ® | Bug Barrier | Deltamethrin | 0.03 |
| Amdro Quick Kill ® | Lawn & Landscape Insect Killer | Zeta-cypermethrin | 0.35 |
| Ortho ® | Bug B Gon | Bifenthrin | 0.3 |
|  |  | Zeta-cypermethrin | 0.075 |
| Natria ® | Insect, Disease & Mite Control | Sulfur | 10 |
|  |  | Pyrethrin | 0.25 |
| Bayer Advanced ® | Complete Insect Killer | Imidacloprid | 0.72 |
|  |  | Beta-cyfluthrin | 0.36 |
| Ortho ® | Flower, Fruit & Vegetable Insect Killer | Acetamiprid | 0.006 |
| Sevin ® | GardenTech | Carbaryl | 0.126 |
| EcoSmart ® | Organic Home Pest Control | 2-phenethyl propionate | 5 |
|  |  | Clover oil | 0.5 |
|  |  | Rosemary oil | 0.5 |
|  |  | Thyme oil | 0.25 |

TABLE 2-continued

Commercially available pesticides tested in laboratory bioassay.

| Trademark | Product | Active Ingredient (AI) | C %* |
|---|---|---|---|
| EcoSmart ® | Organic Garden Insect Killer | Rosemary oil | 0.5 |
| | | Peppermint oil | 0.5 |

*Aqueous solution.

TABLE 3

Ovicidal toxicity of MB to three species of insect eggs

| Insect | n* | $LC_{50}$ (95% CL) mg/cm$^2$ | $LC_{95}$ (95% CL) mg/cm$^2$ | Slope ± SE |
|---|---|---|---|---|
| H. halys | 270 | 0.020 (0.012-0.026) | 0.048 (0.036-0.090) | 4.36 ± 1.11 |
| M. sexta | 270 | 0.015 (0.011-0.020) | 0.060 (0.042-0.112) | 2.77 ± 0.46 |
| P. xylostelta | 2100 | 0.001 (0.001-0.002) | 0.005 (0.004-0.025) | 7.32 ± 1.14 |

*Number of eggs tested.

TABLE 4

Ovicidal effect of MB and tested commercially available pesticides on different species of eggs after 10 days exposure

| Treatment* | AI Dose (mg/cm$^2$) | Hatchability (%) (mean ± SE) | | |
|---|---|---|---|---|
| | | H. halys** | M. sexta** | P. xylostella** |
| Blank Control**** | 0.0000 | 70 ± 5.8$^d$ | 87 ± 8.8$^c$ | 78 ± 3.8$^d$ |
| MB 0.025%**** | 0.0016 | 67 ± 8.8$^d$ | 67 ± 8.8$^c$ | 38 ± 5.5$^c$ |
| MB 0.05%**** | 0.0032 | 63 ± 17.6$^{cd}$ | 63 ± 8.8$^c$ | 13 ± 5.0$^{ab}$ |
| MB 0.1%**** | 0.0064 | 60 ± 10.0$^{cd}$ | 50 ± 17.3$^c$ | 0 ± 0.3$^a$ |
| MB 0.25%**** | 0.0159 | 43 ± 6.7$^{abcd}$ | 40 ± 15.3$^c$ | 1 ± 0.0$^a$ |
| MB 0.5%**** | 0.0318 | 17 ± 12.0$^{ab}$ | 20 ± 10.0$^{abc}$ | 0 ± 0.0$^a$ |
| MB 1%**** | 0.0637 | 0 ± 0.0$^a$ | 3 ± 3.35$^{ab}$ | 0 ± 0.0$^a$ |
| MB 2%**** | 0.1273 | 0 ± 0.0$^a$ | 0 ± 0.0$^a$ | |
| MB 4%**** | 0.2546 | 0 ± 0.0$^a$ | 0 ± 0.0$^a$ | |
| Bug Stop (γ-cyhalothrin) | 0.0016 | 83 ± 8.8$^d$ | 0 ± 0.0$^a$ | 9 ± 5.4$^a$ |
| Carpenter Ant & Termite Killer Plus (β-cyfluthrin) | 0.1592 | 3 ± 3.3$^a$ | 0 ± 0.0$^a$ | 7 ± 1.2$^a$ |
| Bedbug & Flea Home Insect Killer (λ-Cyhalothrin) | 0.0019 | 53 ± 3.3$^{bcd}$ | 0 ± 0.0$^a$ | 2 ± 0.9$^a$ |
| Bug Barrier (Deltamethrin) | 0.0019 | 10 ± 5.8$^{ab}$ | 0 ± 0.0$^a$ | 3 ± 1.0$^a$ |
| Lawn & Landscape Insect Killer (ζ-cypermethrin) | 0.0223 | 0 ± 0.0$^a$ | 0 ± 0.0$^a$ | 1 ± 0.9$^a$ |
| Bug B Gon (Bifenthrin & ζ-cypermethrin) | 0.0239 | 33 ± 14.5$^{abcd}$ | 43 ± 14.5$^c$ | 1 ± 0.7$^a$ |
| Insect, Disease & Mite Control (Sulfur & Pyrethrin) | 0.6525 | 3 ± 3.3$^a$ | | |
| Complete Insect Killer (Imidacloprid & β-cyfluthrin) | 0.0688 | 0 ± 0.00$^a$ | | |
| Flower, Fruit & Vegetable Insect Killer (Acetamiprid) | 0.0004 | 67 ± 20.3$^d$ | | 16 ± 7.0$^{ab}$ |
| GardenTech (Carbaryl) | 0.0080 | 0 ± 0.0$^a$ | | 28 ± 9.2$^{bc}$ |
| Organic Home Pest Control (2-phenethyl propionate & clover oil & Rosemary oil & Thyme oil) | 0.3979 | 17 ± 3.3$^{ab}$ | 30 ± 17.3$^{bc}$ | 1 ± 0.3$^a$ |
| Organic Garden Insect Killer (Rosemary Oil & Peppermint Oil) | 0.0637 | 70 ± 25.2$^d$ | | |

*0.5 ml volume applied.
**30 eggs per treatment.
***300 eggs per treatment.
****DI water solution contained 0.5% Tween 20 (v/v) and 0.5% Tween 80 (v/v).
Means within the same column flowed by the different letters are significantly different at α = 0.05 (Log transformed, N = 3; for H. halys, df = 20, 42, F = 9.41, p < 0.001; for M. sexta, df = 15, 32, F = 14.14, p < 0.001; for P. xylostella, df = 15, 32, F = 29.18, p < 0.001).

We claim:

1. A method for killing insects, ticks, and mites, said method comprising treating an object or area with an insect, tick, and mite killing effective amount of a composition comprising methyl benzoate, an emulsifier, and optionally a carrier; wherein methyl benzoate is the sole insecticide in said composition and wherein methyl benzoate is the sole chemical component of an essential oil in said composition; wherein said insects are selected from the group consisting of blood-sucking insects, biting insects, and insects that are harmful to agricultural plants; wherein said insects are not in the family Vespidae and wherein said insects are not wasps, yellowjackets, or hornets.

2. The method according to claim 1, wherein said carrier is water.

3. The method according to claim 1, wherein said method consists essentially of treating an object or area with an insect, tick, and mite killing effective amount of a composition consisting essentially of methyl benzoate, an emulsifier, and optionally a carrier.

4. The method according to claim 1, wherein said method consists of treating an object or area with an insect, tick, and mite killing effective amount of a composition consisting of methyl benzoate, an emulsifier, and optionally a carrier.

5. The method according to claim 1, wherein said insects are selected from the group consisting of Drosophila suzukii, Halyomorpha halys, Plutella xylostella, and Manduca sexta.

6. The method according to claim 1, wherein said insects are insects harmful to agricultural plants.

7. The method according to claim 6, wherein said insects harmful to agricultural plants are selected from the group consisting of spotted wing drosophila Drosophila suzukii, brown marmorated stinkbug Halyomorpha halys, emerald ash borer Agrilus planipennis, gypsy moth Lymantria dispar, pink hibiscus mealybug Maconellicoccus hirsutus, Mediterranean fruit fly Ceratitis capitata, plum curculio Conotrachelus nenuphar, diamondback moth Plutella xylostella, soybean aphid Aphis glycines, cotton aphid Aphis gossypii, indianmeal moths Plodia interpunctella, bean weevils Acanthoscelides obtectus, mountain pine beetle Dendroctonus ponderosas, and tobacco hornworm Manduca sexta.

8. The method according to claim 1, wherein said ticks are selected from the group consisting of Ornithodorus moubata, Ixodes ricinus, Boophilus microplus, and Amblyomma hebreum.

9. The method according to claim 1, wherein said mites are selected from the group consisting of Varroa destructor,

*Sarcoptes scabiei, Dermanyssus gallinae, Tetranychus urticae, Tetranychus cinnabarinus,* and *Oligonychus pratensis.*

10. The method according to claim 1, wherein said insects are blood-sucking insects.

11. The method according to claim 10, wherein said blood-sucking insects are selected from the group consisting of mosquitoes, sand flies, owl gnats, blackfly, buffalo gnats, biting flies, tsetse flies, horseflies, house flies, meat flies, flies which cause myiasis, bugs, lice, louse flies, fleas, and sand fleas.

12. The method according to claim 10, wherein said blood-sucking insects are selected from the group consisting of *Aedes* species, *Culex* species, *Anopheles* species, *Phlebotomus* species, *Lutzomyia* species, *Phlebotomus papatasi, Phlebotoma* species, *Culicoides* species, *Simulium, Stomoxys calcitrans, Glossina* species, *Tabanus* species, *Haematopota* species, *Chrysops* species, *Musca domestica, Fannia canicularis, Sarcophaga carnaria, Lucilia cuprina, Chrysomyia chloropyga, Hypoderma bovis, Hypoderma lineatum, Dermatobia hominis, Oestrus ovis, Gasterophilus intestinalis, cochliomyia hominovorax, Cimex lectularius, Rhodnius prolixus, Triatoma infestans, Pediculus humaanus, Haematopinus suis, damalina ovis, Melaphagus orinus, Pulext irritans, Cthenocephalides canis, Xenopsylla cheopis,* and *Dermatophilus penetrans.*

13. The method according to claim 1, wherein said insects are biting insects.

14. The method according to claim 1, Wherein said biting insects are selected from the group consisting of cockroaches, beetles, termites, and bed bugs.

15. The method according to claim 13, wherein said biting insects are selected from the group consisting of *Blattella germanica, Periplaneta americana, Blatta orientalis, Supella supellectilium, Sitophilus granarius, Tenebrio molitor, Dermestes lardarius, Stegobium paniceum, Anobium puntactum, Hylotrupes bajulus, Reticulitermes lucifugus,* and *Cimex lectularius.*

16. A method for killing insects, said method comprising treating an object or area with an insect killing effective amount of a composition comprising methyl benzoate, an emulsifier, and optionally a carrier; wherein methyl benzoate is the sole insecticide in said composition and wherein methyl benzoate is the sole chemical component of an essential oil in said composition; wherein said insects are insects harmful to agricultural plants; wherein said insects are not in the family Vespidae and wherein said insects are not wasps, yellowjackets, or hornets.

17. The method according to claim 16, wherein said insects harmful to agricultural plants are selected from the group consisting of spotted wing drosophila *Drosophila suzukii,* brown marmorated stinkbug *Halyomorpha halys,* emerald ash borer *Agrilus planipennis,* gypsy moth *Lymantria dispar,* pink hibiscus mealybug *Maconellicoccus hirsutus,* Mediterranean fruit fly *Ceratitis capitata,* plum curculio *Conotrachelus nenuphar,* diamondback moth *Plutella xylostella,* soybean aphid *Aphis glycines,* cotton aphid *Aphis gossypii,* indianmeal moths *Plodia interpunctella,* bean weevils *Acanthoscelides obtectus,* mountain pine beetle *Dendrocionus ponderosae,* and tobacco hornworm *Manduca sexta.*

18. A method for killing insects, ticks, and mites, said method comprising treating an object or area with an insect, tick, and mite killing effective amount of a composition comprising methyl benzoate, an emulsifier, and optionally a carrier; wherein methyl benzoate is the sole insecticide in said composition and wherein methyl benzoate is the sole chemical component of an essential oil in said composition; wherein said insects are selected from the group consisting of blood-sucking insects, biting insects, and insects that are harmful to agricultural plants; wherein said insects harmful to agricultural plants are selected from the group consisting of spotted wing drosophila *Drosophila suzukii,* brown marmorated stinkbug *Halyomorpha halys,* emerald ash borer *Agrilus planipennis,* gypsy moth *Lymantria dispar,* pink hibiscus mealybug *Maconellicoccus hirsutus,* Mediterranean fruit fly *Ceratitis capitata,* plum curculio *Conotrachelus nenuphar,* diamondback moth *Plutella xylostella,* soybean aphid *Aphis glycines,* cotton aphid *Aphis gossypii,* indianmeal moths *Plodia interpunctella,* bean weevils *Acanthoscelides obtectus,* mountain pine beetle *Dendroctonus ponderosae,* or tobacco hornworm *Manduca sexta*; wherein said ticks are selected from the group consisting of *Ornithodorus moubata, Ixodes ricinus, Boophilus microplus,* or *Ambyomma hebreum*; wherein said mites are selected from the group consisting of *Varroa destructor, Sarcoptes scabiei, Dermanyssus gallinae, Tetranychus urticae, Tetranychus cinnabarinus,* and *Oligonychus pratensis*; wherein said blood-sucking insects are selected from the group consisting of *Aedes* species, *Culex* species, *Anopheles* species, *Phlebotomus* species, *Lutzomyia* species, *Phlebotomus papatasi, Phlebotoma* species, *Culicoides* species, *Simulium, Stomoxys calcitrans, Glossina* species, *Tabanus* species, *Haematopota* species, *Chrysops* species, *Musca domestica, Fannia canicularis, Sarcophaga carnaria, Lucilia cuprina, Chrysomyia chloropyga, Hypoderm bovis, Hypoderma lineatum, Dermatobia hominis, Oestrus ovis, Gasterophilus intestinalis, Cochliomyia hominovorax, Cimex lectularius, Rhodnius prolixus, Triatoma infestans, Pediculus humanus, Haematopinus suis, Damalina ovis, Melaphagus orinus, Pulex irritans, Cthenocephalides canis, Xenopsylla cheopis,* and *Dermatophilus penetrans*; and wherein said biting insects are selected from the group consisting of *Blattella germanica, Periplaneta americana, Blatta orientalis, Supella supellectilium, Sitophilus granarius, Tenebrio molitor, Dermestes lardarius, Stegobium paniceum, Anobium puntactum, Hylotrupes bajulus, Reticulitermes lucifugus,* and *Cimex lectularius.*

\* \* \* \* \*